US009939424B2

(12) United States Patent
Bridgman et al.

(10) Patent No.: US 9,939,424 B2
(45) Date of Patent: Apr. 10, 2018

(54) METHOD FOR GENERATING MICROSCOPIC PATTERNS OF PROTEIN AND OTHER MACROMOLECULES

(71) Applicant: Washington University, Saint Louis, MO (US)

(72) Inventors: Paul C Bridgman, Clayton, MO (US); Stephen G Turney, Newton, MA (US)

(73) Assignee: Washington University, Saint Louis, MO (US)

( * ) Notice: Subject to any disclaimer, the term of this patent is extended or adjusted under 35 U.S.C. 154(b) by 320 days.

(21) Appl. No.: 14/550,353

(22) Filed: Nov. 21, 2014

(65) Prior Publication Data

US 2015/0093818 A1    Apr. 2, 2015

Related U.S. Application Data

(62) Division of application No. 11/930,063, filed on Oct. 30, 2007, now Pat. No. 8,921,283.

(60) Provisional application No. 60/855,299, filed on Oct. 30, 2006.

(51) Int. Cl.
| | |
|---|---|
| *G01N 33/483* | (2006.01) |
| *G03F 7/085* | (2006.01) |
| *G03F 7/09* | (2006.01) |
| *C12M 1/22* | (2006.01) |
| *B01J 19/00* | (2006.01) |
| *C40B 50/18* | (2006.01) |

(52) U.S. Cl.
CPC ...... *G01N 33/4833* (2013.01); *B01J 19/0046* (2013.01); *C12M 23/10* (2013.01); *C40B 50/18* (2013.01); *G03F 7/085* (2013.01); *G03F 7/09* (2013.01); *B01J 2219/00441* (2013.01); *B01J 2219/00605* (2013.01); *B01J 2219/00612* (2013.01); *B01J 2219/00637* (2013.01); *B01J 2219/00725* (2013.01); *B01J 2219/00743* (2013.01)

(58) Field of Classification Search
CPC ....................................................... C12M 23/10
See application file for complete search history.

(56) References Cited

U.S. PATENT DOCUMENTS

| | | | | | |
|---|---|---|---|---|---|
| 4,299,921 | A | * | 11/1981 | Youssef ................. | C12M 23/10 215/348 |
| 4,321,330 | A | * | 3/1982 | Baker .................... | C12M 23/10 435/305.1 |
| 4,775,628 | A | * | 10/1988 | Takakura ............... | C12M 23/10 435/305.4 |

(Continued)

*Primary Examiner* — Jonathan M Hurst
(74) *Attorney, Agent, or Firm* — Zackson Law LLC; Saul L. Zackson

(57) ABSTRACT

Methods and apparatuses for generating microscopic patterns of macromolecules such as proteins on a solid surface are described. Pulsed laser light is used to alter surface portions of a solid surface substrate in a predetermined pattern by removing macromolecules from surface portions of the substrate where the light is focused. The same wavelength light at lower intensity can be used to visualize the removal by its reflection from the specimen surface along the path to the detector. Select macromolecules introduced to the substrate selectively adhere to select surface portions, thereby depositing macromolecules in the predetermined pattern on the solid surface.

7 Claims, 13 Drawing Sheets

(56) References Cited

U.S. PATENT DOCUMENTS

| | | | | |
|---|---|---|---|---|
| 4,902,456 A | * | 2/1990 | Yen | B01D 67/003 |
| | | | | 210/500.23 |
| 5,817,509 A | * | 10/1998 | Stevens | C12M 23/12 |
| | | | | 435/297.5 |
| 2003/0186429 A1 | * | 10/2003 | Goff | C12M 23/10 |
| | | | | 435/305.2 |

* cited by examiner

CULTURE DISH LID WITH DROPPED CENTER

SIDE VIEW OF LID

METHOD FOR GENERATING MICROSCOPIC PATTERNS OF PROTEIN AND OTHER MACROMOLECULES

CROSS-REFERENCE TO RELATED APPLICATIONS

This application is a division of U.S. patent application Ser. No. 11/930,063 filed on Oct. 30, 2007, which claims benefit under 35 U.S.C. § 119(e) to U.S. Provisional Application Ser. No. 60/855,299 filed on Oct. 30, 2006. These applications are incorporated herein by reference, each in its entirety.

STATEMENT REGARDING FEDERALLY SPONSORED RESEARCH OR DEVELOPMENT

This invention was made with government support under NS026150. The government has certain rights in the invention.

FIELD

The present teachings generally relate to multiphoton laser light-induced microscopic patterns of macromolecules.

BACKGROUND

Cell culture studies of neuronal outgrowth and growth cone guidance are facilitated by the ability to engineer micropatterned substrates (Fedoroff, S. and Richardson, A., Protocols for Neur. Cell Cult., pp. 384, 2001). One approach is soft lithography using an elastomeric material such as polydimethylsiloxane (PDMS) to cast stamps on silicon wafers that are patterned by conventional lithographic methods. The PDMS stamp is coated with a solution of molecules and then pressed directly onto surfaces to be patterned. Patterns can be made using many different materials, for example, proteins and alkanethiols.

An uncoated PDMS stamp can also be placed directly on a surface to pattern the binding of a solution of molecules. The stamp may then be removed to allow binding of a second solution of molecules in the remaining bare areas. This approach was first developed by Bonhoeffer (Vielmetter, J., et al., Exp. Brain. Res. 81:283-7, 1990) and used to study growth cone dynamics at borders between laminin and fibronectin (Gomez, T. M. and Letourneau, P. C., J. Neurosci. 14:5959-72, 1994). A similar method was developed for studies of myosin II activity in growth cones at borders between laminin and poly-ornithine (Turney, S. G. and Bridgman, P. C., Nat. Neurosci. 8:717-9, 2005).

Although soft lithography methods are promising, a number of problems remain to be solved. Registration is an issue for multilayer fabrication due to distortion that is intrinsic to elastomeric materials. To limit defects arising from dust particles fabrication must be performed in a clean room environment. Another issue is maximizing the transfer of molecules from the stamp to the surface. Finally, patterns cannot be altered dynamically due to the time it takes to create or modify a stamp.

Maskless fabrication methods offer the possibility of modifying patterns faster and at less cost than methods based on conventional photolithography. One such method is to "print" proteins on a coated glass surface using inkjet printer technology. Proteins such as extracellular matrix (ECM) components, antibodies, enzymes or receptors are deposited in picoliter droplets, requiring less protein than is used in traditional microtitre dish assays. However, the proteins often lose their biological activity as a result of being dried on the glass surface.

Investigations into the mechanisms underlying cellular behavior such as growth and differentiation are enhanced by the ability to control the environment at a microscopic level. Molecules such as proteins that are known to affect cellular behavior can be laid down in patterns on glass or plastic surfaces. However, the patterns are often fixed and are limited in terms of the detail, complexity and spatial resolution that can be achieved. Photolithography methods are somewhat more flexible and have been used to create patterns of macromolecules (Herbert, C. B., et al., Chem. Biol. 4:731-7, 1997; Kleinfeld, D., et al., J. Neurosci. 8:4098-120, 1988). Nevertheless these methods are time consuming, and a need remains for improved methods to create complex micropatterns and micropatterns that can be modified rapidly in response to changing experimental demands. In particular, methods are needed for generating micropatterns of macromolecules on a substrate in the presence of living cells.

Illumination of cells with laser light through a microscope is facilitated with the use of appropriate culture dishes and lids. Some previous designs of culture dish lids include lids which, while reducing condensation, require laser light to pass through plastic, which can distort the optics or absorb the laser light in an undesirable manner (Turney, S. G. and Bridgman, P. C. 2005. Nature Neurosci. 8:717-719).

SUMMARY

The inventors have succeeded in developing novel methods and apparatuses for generating microscopic patterns of macromolecules, such as proteins or nucleic acids, on a solid surface such as a glass slide in the presence or absence of living cells.

In one aspect, the present teachings include a solid surface providing a substantially planar substratum, such as glass, and a multiphoton laser-induced micropattern of macromolecules on the solid surface. The macromolecules, for example, have a plurality of spatial features formed by unbinding a first group of macromolecules from one or more selected regions of the coated solid substrate by exposing the selected regions of the substrate to multiphoton laser energy, and by binding a second group of macromolecules in one or more unselected regions of the solid substrate. In various aspects and embodiments the macromolecules can include proteins, nucleic acids, and fluorophores. For example, macromolecules that cam be micropatterned according to the methods described herein include oligopeptides, polypeptides, lipoproteins, glycoproteins, antibodies, oligonucleotides, laminins, fluorescein, cy2, cy3, alexa-488, alexa 555 and alexa-594.

In another aspect, the invention embraces a method of creating a micropattern of macromolecules on a solid substrate comprising: applying a coating of adhesive molecules to the solid substrate; binding a plurality of macromolecules to the coating of adhesive molecules; and applying incident multiphoton laser light to one or more selected surface areas of the solid substrate to unbind am amount of macromolecules from the selected surface areas to create a micropattern of macromolecules. The method can further comprise applying incident multiphoton laser light to selected surface areas of the solid substrate to directly modify the molecular binding properties of the macromolecules in said selected surface areas. In an exemplary embodiment, the multiphoton laser-induced pattern of macromolecules comprise one or more types of macromolecules hound to adhesive molecules. The adhesive molecules comprise at least one compound promoting adhesion of macromolecules such as proteins, nucleic acids, or live cells to glass surfaces. The adhesive molecules are, for example, antibodies, protein-A, laminin, streptavidin, nucleic acids, poly-lysine or poly-ornithine.

In another aspect, the invention embraces a substrate for cells in culture comprising a glass surface having a coating of adhesive molecules and as plurality of macromolecules hound thereto with or without a predefined micropattern.

In various aspects the incident laser light comprises, for example, ultrafast pulsed near-infrared (IR) light. In one embodiment, applying incident multiphoton laser light to one or more selected surface areas of the solid substrate comprises directing the ultrafast pulsed IR to the selected surface areas along an incident light path of a multiphoton microscope so that the macromolecules are unbound front the adhesive molecules in selected surface areas of the substrate. Directing incident light to the discrete regions can comprise, for example, directing separate beams of incident light to the regions to illuminate the surface areas within the corresponding discrete regions. Directing light to the discrete regions can also comprise serially directing light to each discrete region to separately illuminate each surface portion within a corresponding one of the discrete regions. Directing incident ultrafast pulsed IR light can include scanning the substrate with the incident light to thereby sequentially illuminate separate surface areas of the substrate in the in-focus plane. Scanning the substrate can include changing the intensity of the incident ultrafast pulsed IR light to thereby selectively illuminate a subset of the surface areas of said substrate at high intensity.

In another embodiment, a micropatterned substrate can be produced according to the method in the presence of living cells on the substrate surface. The living cell types can include, but are not limited to, neurons.

In another aspect, the invention embraces a cell culture dish lid for use with a cell culture dish, said lid having a dropped-center well configured for immersion in culture media contained in the cell culture dish and a plurality of perforations. Various embodiments provide for limiting condensation and evaporation by the cell culture dish lid such as a watertight seal such as a silicone seal along the periphery, a tetrafluoroethylene-co-hexafluoropropylene (FEP) membrane covering the perforations, and a liquid reservoir.

In another aspect, the invention embraces an apparatus for generating a micropatterned substrate, said apparatus having: a multiphoton laser, optical elements configured for directing incident light from an ultrafast pulsed multiphoton laser to one or more discrete regions substantially planar substratum comprising, at least one macromolecule. In some aspects, an apparatus can thither include the above mentioned cell culture dish lid.

Other objects an features will be in part apparent and in part pointed out hereinafter.

BRIEF DESCRIPTION OF THE DRAWINGS

Those of skill in the art will understand that the figures, described below, are for illustrative purposes only. The figures are not intended to limit the scope of the present teachings in any way.

DETAILED DESCRIPTION OF THE INVENTION

Figure 1:
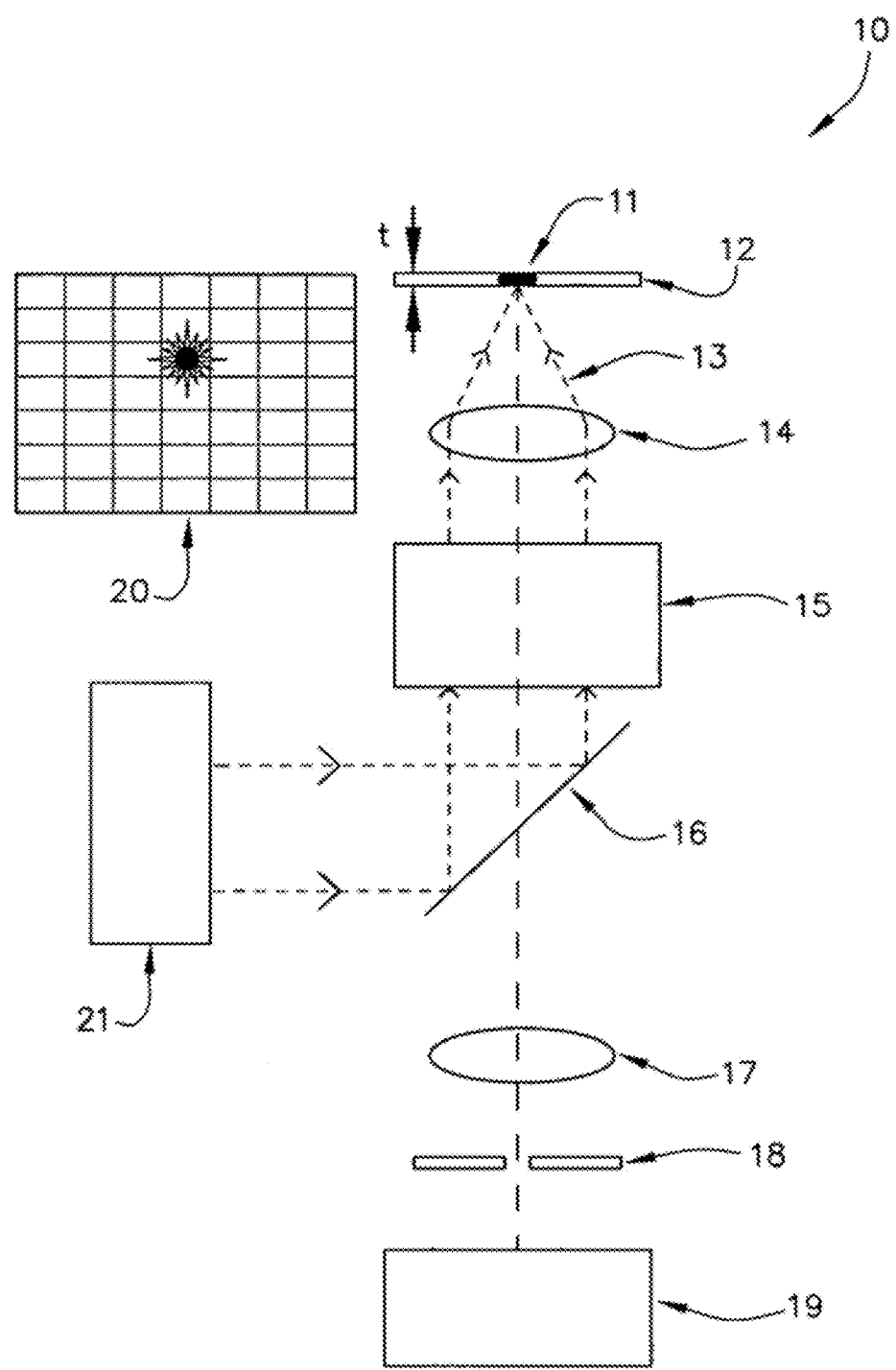
FIG. 1 is a schematic of a reflected light multiphoton scanning microscope of the present invention showing incident light being focused on a glass surface.

The present methods and materials teach a novel approach for creating patterns of macromolecules on as solid substrate surface using a microscope and multiphoton incident laser light. The method is maskless and is based on unbinding of macromolecules using the incident light. Previous work has shown that fluorescently tagged ligands can be unbound from receptors using high-intensity visible-wavelength illumination (Akaaboune, M., et al., Neuron 34:865-76, 2002). However, visible wavelengths are not readily absorbed by unlabeled proteins. The present teachings are based in part on the new discovery that multiphoton excitation is able to unbind unlabeled macromolecules. In addition, rebinding can occur at sites where macromolecules are unbound from a surface by multiphoton excitation. This patterning method is dynamic and operable on a submicron scale of manufacture. As it is also amenable to use with living cells this method can allow basic research investigations into cellular growth and function in addition to creating co-cultures of multiple cell types, tissue engineering, and fabrication of biosensor and protein microarrays.

As used herein, the term "micropattern" refers to patterns generated by the alternating, presence and absence of densely located fine lines and geometrical elements at a submicron scale or larger. Broadly, a micropattern can include any configuration of macromolecules on a substrate that serves to limit or guide the activity of cells on the substrate, wherein the configuration is not limited to any particular shape or form.

As used herein, the term "macromolecule" refers broadly to any polymer encompassing, but not limited to, a protein, a polypeptide, cofactors, a polysaccharide, an antibody, or a nucleic acid including RNA and DNA, as well as various antigens, and lipids. "Protein" as used herein can also encompass a glycoprotein or as lipoprotein.

As used herein, the term "multiphoton laser-induced" refers to that characteristic of a micropattern of macromolecules that has been established on a solid substrate in whole or in part through application of multiphoton laser light to the solid surface.

In brief, the incident laser light is directed to selected surface areas of the solid substrate. The incident laser light modifies the binding of macromolecules to the selected surface areas resulting in their release or unbinding. The result in any case is that macromolecules remain bound to the solid substrate in unselected surface areas of the substrate. The surface areas that receive incident laser light are selected according to the desired micropattern, which leaves the unselected surface areas as the negative micropattern formed by illuminating the selected areas. Macromolecules such as proteins remain hound to the unselected areas (i.e. forming the negative micropattern), thus establishing a micropattern of the macromolecules bound to the solid substrate. The macromolecules that are bound to the solid substrate, either directly to the substrate material or to the adhesive molecules, serve to limit or guide the activity of cells placed on the solid substrate.

Use of incident laser light allows selection and modification of the selected surface areas at a relatively high spatial resolution, and also allows the user to rapidly establish new micropatterns on a solid substrate on which cells have previously been established and are under observation under microscope. The present methods and materials therefore provide a novel way in which to dynamically create complex micropatterns of macromolecules, wherein the micropatterns have a high degree of spatial resolution.

The way in which the selected surface areas are modified by the incident laser light to affect the binding characteristics of the selected surface areas can vary. In an exemplary embodiment a glass slide or coverslip is used as the solid substrate. Alternatively, a flexible yet solid surface such as a strip of Sylgard can be used.

Unbinding of macromolecules from the solid substrate, and other surface modifications of the solid substrate, vary nonlinearly with laser intensity. Intensities adequate for the intended unbinding will therefore vary. For example, using a multiphoton microscope, a suitable intensity at the back focal plane of the objective is at least about 80 mW (average power, not peak pulse power) at a wavelength of about 800 nm. However, the intensity required to unbind can vary depending on: the selected wavelength, the IR efficiency of the objective, and the type of macromolecule to be unbound. For example, higher excitation power is used for unbinding of unlabeled macromolecules than for fluorescently labeled molecules. Any factor or factors that combine to produce an eight-fold, or greater, reduction of power between the back focal plane of the objective and the substrate surface can result in no unbinding. The unbinding effect is also likely wavelength dependent because the targeted macromolecule must absorb the incident IR light to be unbound. However, wavelength dependence is difficult to predict because multiphoton excitation is nonlinear. In any case, the amount of unbinding can be increased by scanning an area multiple times or by increasing the exposure time at each pixel. At very high excitation powers, damage to the substrate or macromolecule can occur, limiting the amount of unbinding and/or the subsequent binding by a different macromolecule. In various aspects the incident multiphoton laser light is provided in femtosecond pulses in the near-infrared light spectrum (750-1000 nm)

In one embodiment, the solid substrate is coated directly with a macromolecule. The macromolecules bound to the solid substrate serve to limit or guide the activity of cells placed on the solid substrate. For example, a solid substrate is coated with a protein such as laminin-1 (LN-1) which directs or limits the outgrowth of neurons. The process of applying a macromolecule to the solid substrate is generally well known (see generally, Immunocytochemical Methods and Protocols (Methods in Molecular Biology), Lorette C. Javois, 1999, Humana Press, ISBN-13: 978-0896035706). In various aspects the substrate is coated by immersion in an aqueous solution of the macromolecule, rinsing, to remove unbound macromolecules and then keeping the substrate hydrated.

The solid substrate with a coating of macromolecules, for example a protein coating, bound thereto, is positioned in a suitably configured microscope. Incident laser light is directed through the microscope optical elements to selected surface areas of the solid substrate. The incident laser light unbinds the macromolecules from the solid substrate, but only in the discrete, selected surface areas. By choosing the selected surface areas according to the reverse of the desired micropattern, and directing the incident laser light only to the selected surface areas, thus is formed a micropattern of macromolecules bound to the solid substrate. Depending in the chosen micropattern, it can then function as a type of channel, barrier, maze or the like that guides or limits the outgrowth or movement of cells placed on the solid substrate. Also depending on the experimental requirements, the macromolecules can be unlabeled, or can be advantageously labeled with dyes or markers such as fluorescent dyes that can be used to optically mark the micropattern. Micropatterns can be created that employ both labeled and unlabeled macromolecules wherein the labeled and unlabeled macromolecules occupy different, complementary surface areas on the solid substrate.

In another embodiment, the solid substrate is first coated with adhesive molecules to form an adhesive substrate. The term "adhesive" is used broadly to encompass any characteristic of a molecule that results in binding, adhering, hybridizing or bonding of one or more other molecules to the adhesive molecule. The adhesive molecules serve an anchoring function for other macromolecules that are then bound to the adhesive substrate. The macromolecules bound to the adhesives serve to limit or guide the activity of cells placed on the solid substrate. The selection of an adhesive can vary according to the selection of macromolecules that ultimately will be bound to the adhesives, as described further in examples herein. The adhesive molecules can be made, for example, of poly-lysine, poly-ornithine, chrom-gelatin (chrom-alum gelatin), a protein, or any other like molecules with the ability to bind a broad range of macromolecules. Solutions of adhesive and other macromolecules suitable for use according to the present disclosure are known and described elsewhere (see e.g., Turney, S. G. and Bridgman, P. C., Nat. Neurosci. 8:717-9, 2005). Alternatively, adhesion is created using a molecule, or molecules, that is selectively adhesive for a particular molecule or class of molecules, such as a peptide ligand. For example, in one embodiment, a solid substrate can be coated with streptavidin which acts as an adhesive molecule for biotin or any biotinylated molecule, or alternatively a solid substrate with biotin, which acts as an adhesive molecule for streptavidin. For example, in one embodiment a solid substrate is coated with streptavidin and a biotinylated oligonucleotide hound thereto via the interaction of the biotin with streptavidin. The biotinylated oligonucleotide can have a specific nucleotide sequence and can serve as an adhesive molecule for oligonucleotides having a complementary nucleotide sequence. Alternatively, antibody interactions can be used advantageously to selectively bind labeled or unlabeled antibody to selected adhesive molecules.

Figure 4:
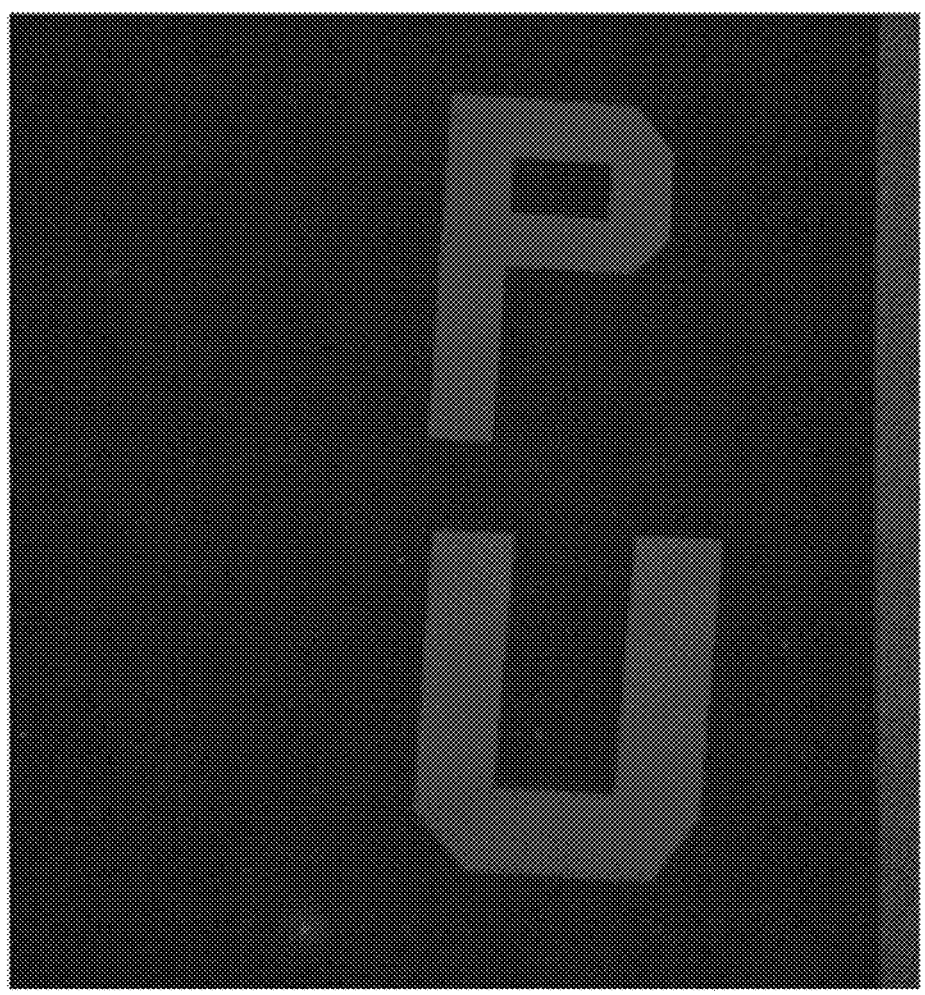
FIG. 4 is an image showing rebinding of cy3-conjugated laminin-after multiphoton laser-induced unbinding of unlabeled laminin-1.

Furthermore, multiple molecules bound to one another in sequence can be employed to establish micropatterns of macromolecules, and the approach can also be used together or in sequence with saturating amounts of other molecules or fluorescent tags or dyes to achieve a desired micropattern having certain optical characteristics (see e.g., FIG. 4).

Once the substrate has been coated with the adhesive molecules to form the adhesive substrate, the adhesive substrate can be exposed to a selected macromolecule or macromolecules that bind non-selectively or selectively. The adhesive substrate with macromolecules bound thereto, can be positioned in a suitably configured microscope. Incident laser light can be directed through the microscope optical elements to selected surface areas of the adhesive substrate. The incident laser light unbinds the macromolecules from the adhesive molecules, but only in the discrete, selected surface areas. By choosing the selected surface areas according to a desired micropattern, and directing the incident laser light only to the selected surface areas, thus is formed a micropattern of macromolecules bound to the adhesive molecules. Depending in the chosen micropattern, it can then function as a type of channel, barrier, maze or the like that guides or limits the outgrowth or movement of cells placed on the solid substrate.

Another way in which the incident laser light affects the binding characteristics of the solid substrate is by direct surface modification of the solid substrate, as occurs separate from unbinding of macromolecules from the solid substrate or from an adhesive molecule. For example, selected surface areas of a glass slide or coverslip are exposed to the incident laser light. The incident laser light directly modifies the surface binding characteristics of the glass material, so that macromolecules bind preferentially to unselected surface areas of the glass slide or coverslip. This technique for modifying the solid substrate can be used alone or together with the technique using adhesive molecules.

A reflected light multiphoton scanning microscope (see e.g. FIG. 1, reference numeral 10) is used for obtaining high resolution images of light reflected or emitted from the surface of a glass microscope slide, or other solid transparent surface that can be used as a substrate, and thriller for generating on the substrate high resolution spatial patterns of organic or inorganic macromolecules such as, but not limited to, proteins or small polypeptides. Generally speaking, microscope 10 illuminates multiple microscopic areas of the substrate. For illustrative purposes, the substrate is as glass coverslip, but can be any suitably transparent solid surface substrate.

A multiphoton microscope is generally configured for creating a pattern of macromolecules on a substrate as described herein as follows: a microscope objective is configured to be spaced a distance from the substrate at which at least part of the substrate is within the in-focus plane of the objective, optical elements of the microscope are configured to direct incident light to discrete regions of the in-focus plane of the objective to illuminate surface areas of the substrate that are within the discrete regions, and a sensor is positioned in the return light path for generating at least one signal representative of the light reflected or emitted from the surface areas of the substrate.

The incident light can be, for example, from an ultrafast pulsed IR laser. In an exemplary embodiment, a multiphoton laser such as a two photon laser is used. A multiphoton laser such as a two photon laser has a suitably high spatial resolution with respect to removing unlabeled macromolecules from the substrate and therefore is well-suited for creating sharply defined patterns of macromolecules. A multiphoton laser is preferred over other types of pulsed lasers because it induces nonlinear (multiphoton) effects due to its extremely high pulse power. This ability of multiphoton lasers stands in contrast to other lithographic or transfer film techniques which use visible wavelength lasers, either pulsed or not pulsed, that have much lower peak pulse power and therefore cannot induce nonlinear effects. In an exemplary embodiment, the light source is therefore a pulsed IR multiphoton laser. FIG. 1 illustrates both an incident light path and a return light path. For simplification the light beam in the return light path has been omitted. However, it is to be understood that the incident and return light paths are present during operation of the microscope 10.

Microscope 10 includes a scanning/de-scanning mechanism 15, a beam splitter 16, an objective 14, as confocal pinhole aperture 18, a light detector 19, and a multiphoton laser oscillator 21. The dimensions of the incident light can be controlled by any means known in the art so that only a precisely defined area of the target substrate is exposed to the light. For example, the light can be focused through an objective to narrow the beam and achieve very tightly spatially controlled modifications of the substrate surface.

Referring again to FIG. 1, incident light 13 is directed along the incident light path to the glass surface via the beam splitter 16, scanning/de-scanning mechanism 15, beam splitter 16 and objective 14. Preferably, the scanning/de-scanning mechanism 15 comprises a raster scan (not shown and suitable lenses (not shown) for serially directing a plurality of collimated incident light beams off the beam splitter 16 and through the objective 14 to serially illuminate different surface areas of the glass slide. The objective 14 focuses the incident light beams onto the glass surface. The light beams emitted from the scanning/de-scanning mechanism 15 are directed to the objective 14 at different angles so that the beams are focused at different areas of the in-focus plane 12 of the objective 14. In other words, the scanning/de-scanning mechanism 15 serially directs incident light to a plurality of discrete regions of the in-focus plane 20.

The scanning/de-scanning mechanism 15 divides the in-focus plane 12 of the objective 14 into a plurality of discrete grid regions 20 (e.g., 512 times 512 grid regions) and serially directs incident light to each grid region. For illustrative purposes, grid regions 20 are shown at enlarged scale. An object tile 11 of the surface that is positioned in a grid region of the in-focus plane 12, absorbs and reflects the incident light. Although the in-focus plane 12 is identified as a plane, it is to be understood that it actually has a thickness proportional to the depth of field of the objective 14. Likewise, each grid region has a thickness t (i.e., a distance from top to bottom as viewed in FIG. 1) preferably proportional to the depth of field of the objective 14. Although the numerical aperture of the objective 14 is preferably 0.9 or higher, it is to be understood it can have some other value.

Several embodiments of the general method of creating a pattern of macromolecules on a substrate using the apparatus as described are possible. The substrate is positioned in the optical field of view and is visualized by reflected light imaging. As described supra, the scanning/de-scanning mechanism 15 divides the in-focus plane 12 of the objective 14 into a plurality of discrete grid regions. The grid regions can be any sort of regular pattern as desired and suitable for guiding and tracking modifications of the substrate surface as they are made. Moreover, any equivalent means of dividing the in-focus plane of the objective of a multiphoton microscope into a plurality of discrete regions conducive to tracking surface modifications is also suitable. In one embodiment, the discrete regions of the in-focus plane of the objective are of a thickness substantially equal to the axial length of the excitation volume and proportional to the depth of field of the objective.

The incident light is then directed to the discrete regions to illuminate only those surface areas of the substrate that are within the discrete regions. This basic maneuver is used to directly modify surface areas of the substrate itself, and can also be use to selectively remove any macromolecules already bound to the substrate via adhesive molecules. More specifically, any macromolecules on each surface portion associated with each discrete region are removed by the incident light at the in-focus plane. The incident light can also directly modify the surface of the substrate material itself. In either case, the surface binding properties of the substrate are modified in the selected regions. The relative amount of binding of macromolecules either to the adhesive molecules or to the substrate material is detected, for example, by visualizing changes in the signal strength of the reflected light image.

Manipulations of the microscope apparatus are used to change the in-focus plane as desired, and new discrete grid regions established in the new plane of focus so that other select regions of the substrate are subject to surface modification by the incident light. Serial manipulations of the microscope apparatus are used to change the in-focus plane, thereby allowing sequential laying out of a pattern as desired using sequential modifications of surface areas of the substrate in each succeeding in-focus plane. In another embodiment, the pattern can also be established in whole or in part by scanning the substrate or a region thereof with light of a different intensity. For example, the substrate surface can be scanned by increasing the intensity of the incident ultrafast pulsed IR light, increasing, the light intensity selectively illuminates a subset of the surface areas of the substrate at high intensity, and the subset of surface areas are selectively modified. The resulting surface modifications affect the binding properties of the surface areas so that any macromolecules subsequently introduced to the substrate selectively bind to the modified surface areas.

Directing incident light to the discrete regions involves, for example, simply directing separate beams of incident light to the discrete regions to illuminate the surface areas within the corresponding discrete regions. In another embodiment, light is serially directed to each discrete region to separately illuminate each surface portion within a corresponding one of the discrete regions.

More specifically, removal of macromolecules from selected surface areas according to a desired pattern can be accomplished as follows. The in-focus plane of the objective is divided into a plurality of grid regions. The substrate is positioned a distance from the objective of the optical apparatus so that surface areas of the substrate are within the grid regions of the in-focus plane. Incident light such as ultrafast pulsed ER light is directed to the grid regions to illuminate the surface areas of the substrate that are within the grid regions. The distance between the substrate and objective is then altered using typical manipulations of the microscope apparatus so that surface areas of the substrate that were previously outside the grid regions of the focal plane, are consequently within previously unoccupied grid regions of the in-focus plane. The incident light is then directed to the grid regions to illuminate the other surface areas of the substrate that are within the previously unoccupied grid regions. In one embodiment, the method further comprises re-positioning the substrate with respect to the objective so that more of the surface areas of the substrate are within the objective's depth of field.

Figure 2:
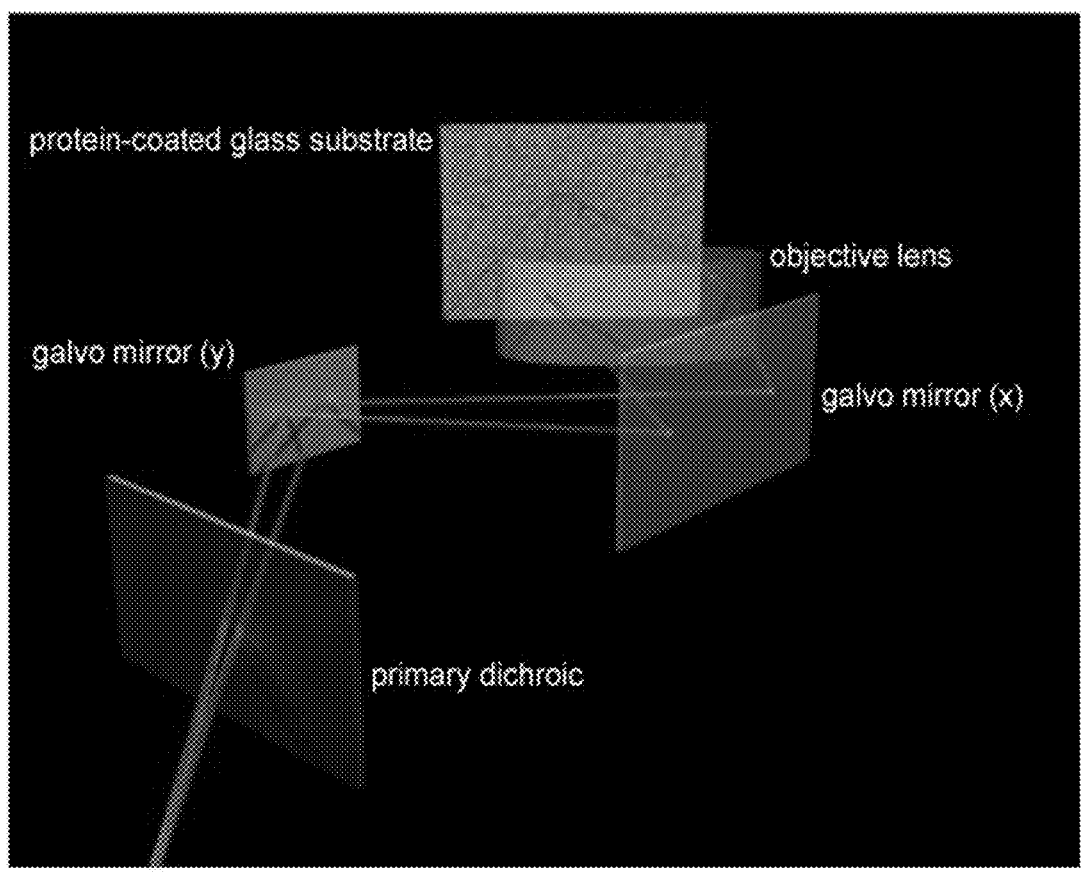
FIG. 2 is a graphical representation of the incident light path shown in FIG. 1.
Figure 3:
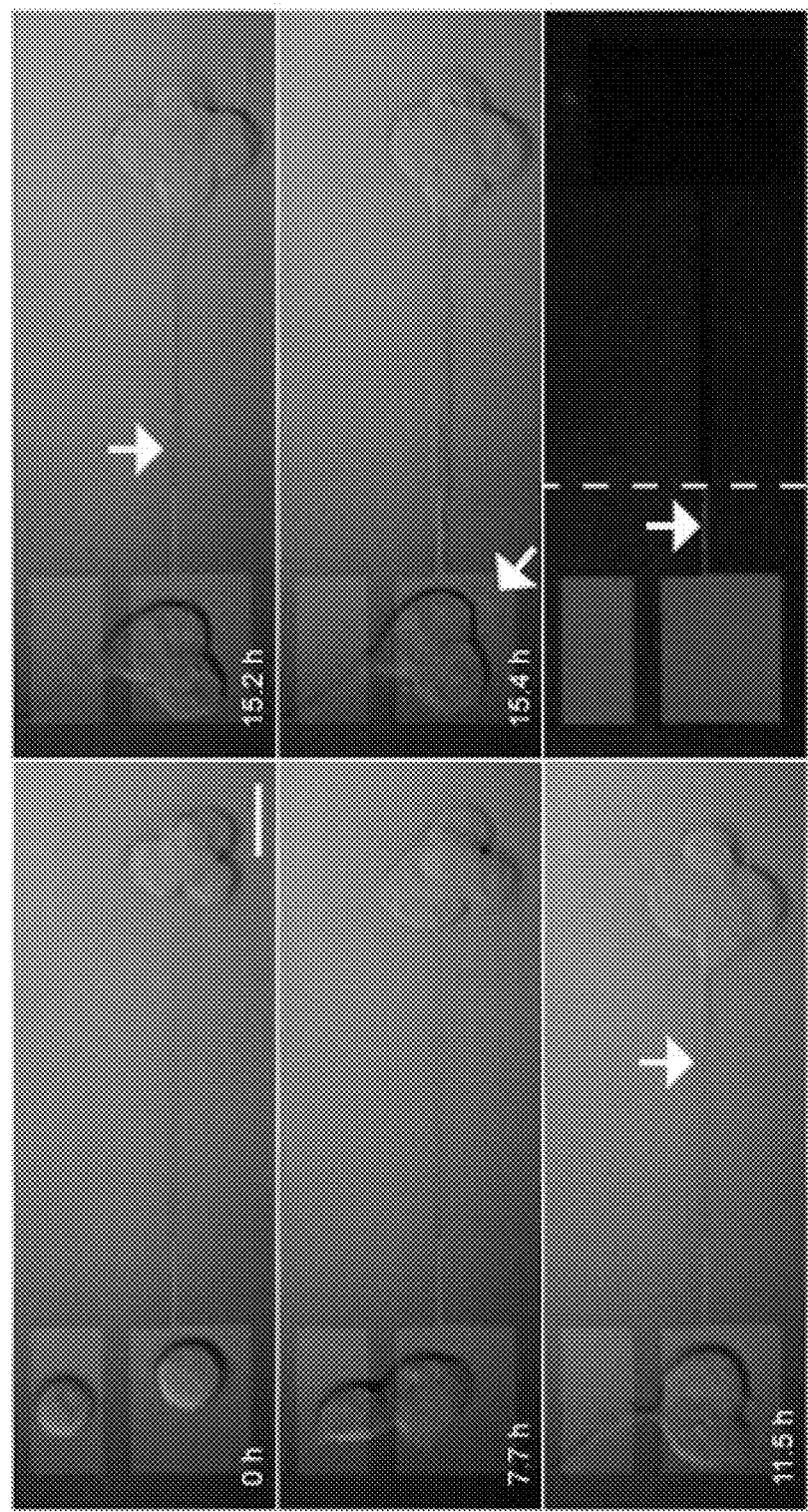
FIG. 3 is a time lapse series showing directed outgrowth of SCG neurons a patterned laminin-1 substrate.

FIG. 2 is a graphical representation of an exemplary incident light path for selectively removing macromolecules, for example a protein, coating the solid substrate surface (i.e removing macromolecules from and adhesive substrate). The pulsed IR light is focused to a diffraction-limited spot on the substrate surface by the objective lens. A scanhead (not shown) includes galvanometer-mounted mirrors (e.g. "galvo mirror (x)" and "galvo mirror (y)" in FIG. 2) configured to be moved in response to an electrical input signal. The galvo mirrors are configured along the light path so that, when moved in unison, they cooperatively direct the locus of the pulsed IR light over the surface of the substrate so that the pulsed IR light scans across the surface of the substrate as directed by deflection off the galvo mirrors. Control of the galvo mirror positions can be readily achieved by computer control. Macromolecules bound to the adhesives, for example, protein macromolecules, are removed from the solid substrate surface where the IR light is focused and thus, as the focal point is shifted by the galvo mirrors, protein is removed along the path of the light where and as the focal point moves. If the solid substrate is transparent and relatively thin (for example a glass coverslip) in comparison to the working distance of the objective lens, the macromolecules (bound to the adhesive molecules) can be on either the front or back surface of the substrate and still be removed according to the method as described. Thus, the protein or other macromolecules bound to the adhesive molecules on the solid substrate surface are selectively removed only from those areas of the substrate surface upon which the IR light is focused.

The resulting surface modified adhesive substrate bears a micropattern of macromolecules according to the immediate specifications of the investigator. If desired, the micropattern can be created by the investigator on the substrate in the optical apparatus simultaneously with observations of cell behavior on the substrate. This permits the investigator to react dynamically to observations of cellular behavior by adding a micropattern to the macromolecular substrate on which cells are already established and being observed.

The detailed description set-forth above is provided to aid those skilled in the art in practicing the present teachings. However, the teachings described and claimed herein are not to be limited in scope by the specific embodiments herein disclosed. Any equivalent embodiments are intended to be within the scope of this invention. Various modifications of the teachings which do not depart from the spirit or scope of the present inventive discoveries, in addition to those shown and described here in, will become apparent to those skilled in the art from the foregoing description. Such modifications are also intended to fall within the scope of the appended claims.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result, without departing from the spirit and scope of the invention.

Example 1

This example illustrates formation of a patterned laminin-1 (LN-1) substrate using the disclosed methods, and directed outgrowth of SCG neurons on the patterned LN-1. As shown in FIG. 1, a LN-1 substrate was produced using a glass coverslip coated with alternating stripes of alexa-594 conjugated LN-1 (light grey boxes highlighted, on the left of each panel), and unlabeled LN-1 (darker grey box highlighted to the right of each panel). The alternating stripes were produced as follows: the solid substrate (a glass coverslip) was first coated in unlabeled LN-1, and then selected areas of the unlabeled LN-1 were unbound (removed) with pulsed IR light according to the methods as described. The substrate with the modified LN-1 surface was then exposed to a solution of the fluorescent alexa-594 conjugated LN-1, and further processed to remove unbound alexa-594 conjugated LN-1. Dissociated SGC neurons were then plated onto the coverslip having the described surface modifications in the specified pattern, and a time-lapse series of images were taken. At 0 hours, multiphoton illumination was used to remove unlabeled LN-1 from around neuron cell bodies, leaving them on small, separate blocks of LN-1. The image in the in the final panel shows the pattern of remaining LN-1. Light grey blocks at left are alexa-594 conjugated LN-1, and the dark block at right is unlabeled, non-fluorescent LN-1. A thin line of LN-1 connects two blocks, changing from light grey (at the arrow; final panel), to dark at the border between stripes of alexa-594 conjugated LN-1 and unlabeled. LN-1 (dashed line; final panel). At 7.7 hours, the neurons do not show any outgrowth of neurites. At 11.5 hours, as neurite is apparent, extending along the thin, line of LN-1 (arrow). At 15.2 hours, the neurite is shown extending farther along the thin line (arrow). By 15.4 hours, the new neurite has reached the cell bodies in the distal block (arrow). Scale bar is 20 µm.

Example 2

This example illustrates a micropatterned substrate surface produced using rebinding of cy3-conjugated laminin-1 after multiphoton laser-induced unbinding of unlabeled laminin-1 (see FIG. 4). A glass slide was used as substrate and uniformly coated with poly-1-ornithine (PLO), then partially masked with a Sylgard strip (at right edge) before receiving a second coating of unlabeled LN-1. A multiphoton laser was then used to unbind LN-1 from the substrate to produce the letters "P" and "U". The Sylgard strip was removed before rebinding in the letter regions with cy3-conjugated LN-1 (light grey).

Example 3

Figure 5:
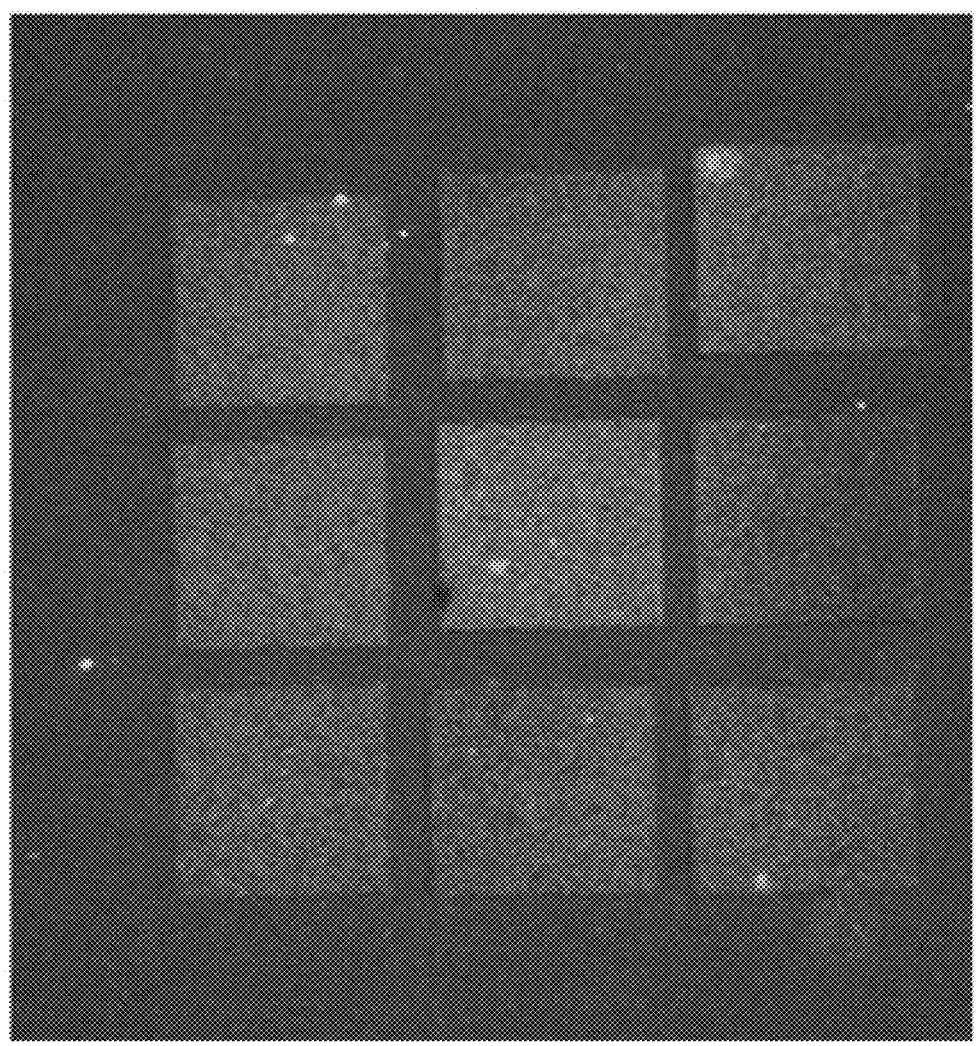
FIG. 5 is an demonstrating multiphoton laser-induced unbinding of fluorescently-tagged streptavidin from biotin on as biotin coated slide.

This example illustrates a multiphoton laser-induced unbinding of fluorescently-tagged streptavidin (SA) to biotin (see FIG. 5). A biotin-coated glass slide was first labeled with a saturating dose of alexa-594 (shown in dark grey). The SA was then unbound from biotin using multiphoton illumination, and alexa-488 SA was added to rebind the biotin to produce the surface grid pattern as shown (light grey).

Example 4

Figure 6:
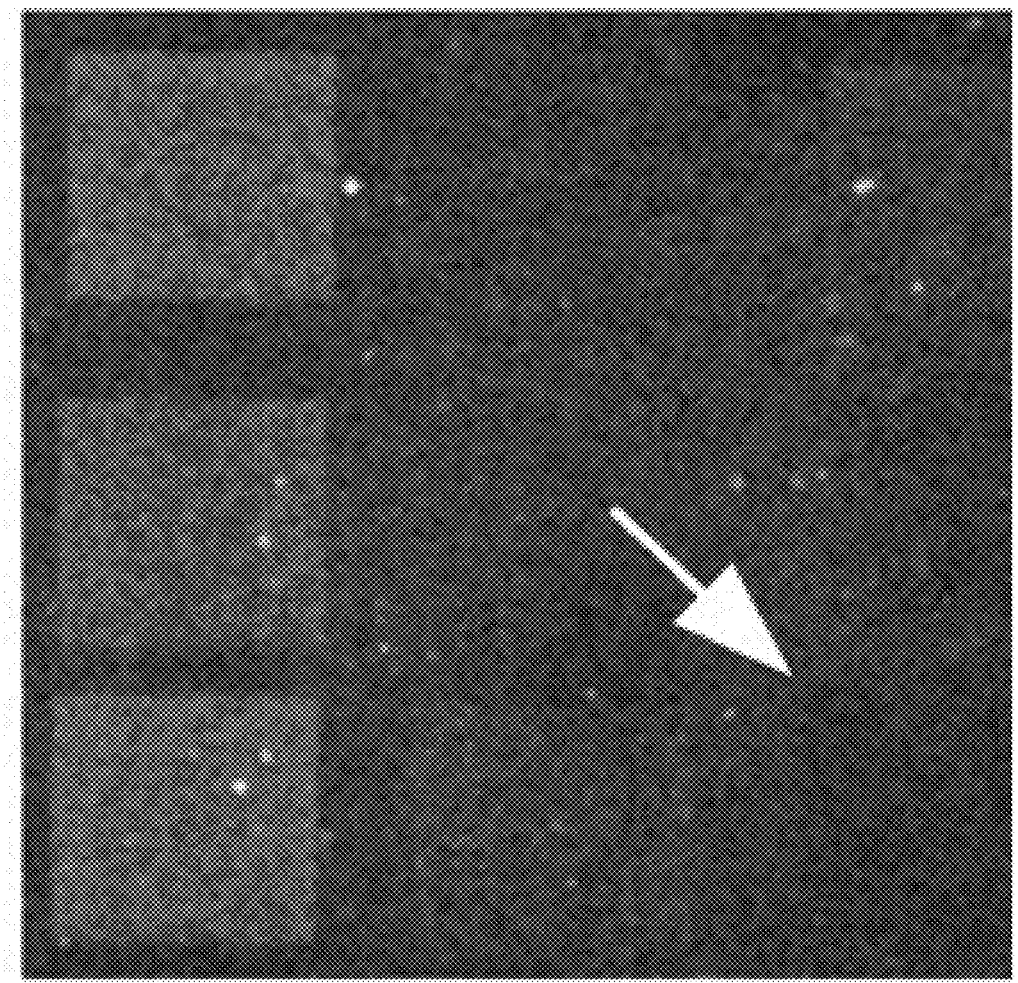
FIG. 6 is an image showing n multiphoton laser-induced unbinding of fluorescently-tagged anti-laminin polyclonal antibody from laminin on a laminin-coated slide.

This example illustrates a multiphoton laser-induced unbinding of polyclonal antibody (pAb) (see FIG. 6). A LN-1-coated slide was labeled with as saturating dose of cy3-conjugated anti-laminin pAb (dark grey). The pAb was unbound from the slide using multiphoton laser illumination, varying, the laser intensity but normalizing the total two-photon fluorescence emission by also varying the illumination time, following the inverse square dependence on laser intensity. The amount of unbinding of pAb was intensity dependent, as is apparent by the amount of rebinding of as cy2-conjugated anti-laminin pAb (light grey). The block that was illuminated at lowest intensity showed the least rebinding (arrow).

Example 5

Figure 7:
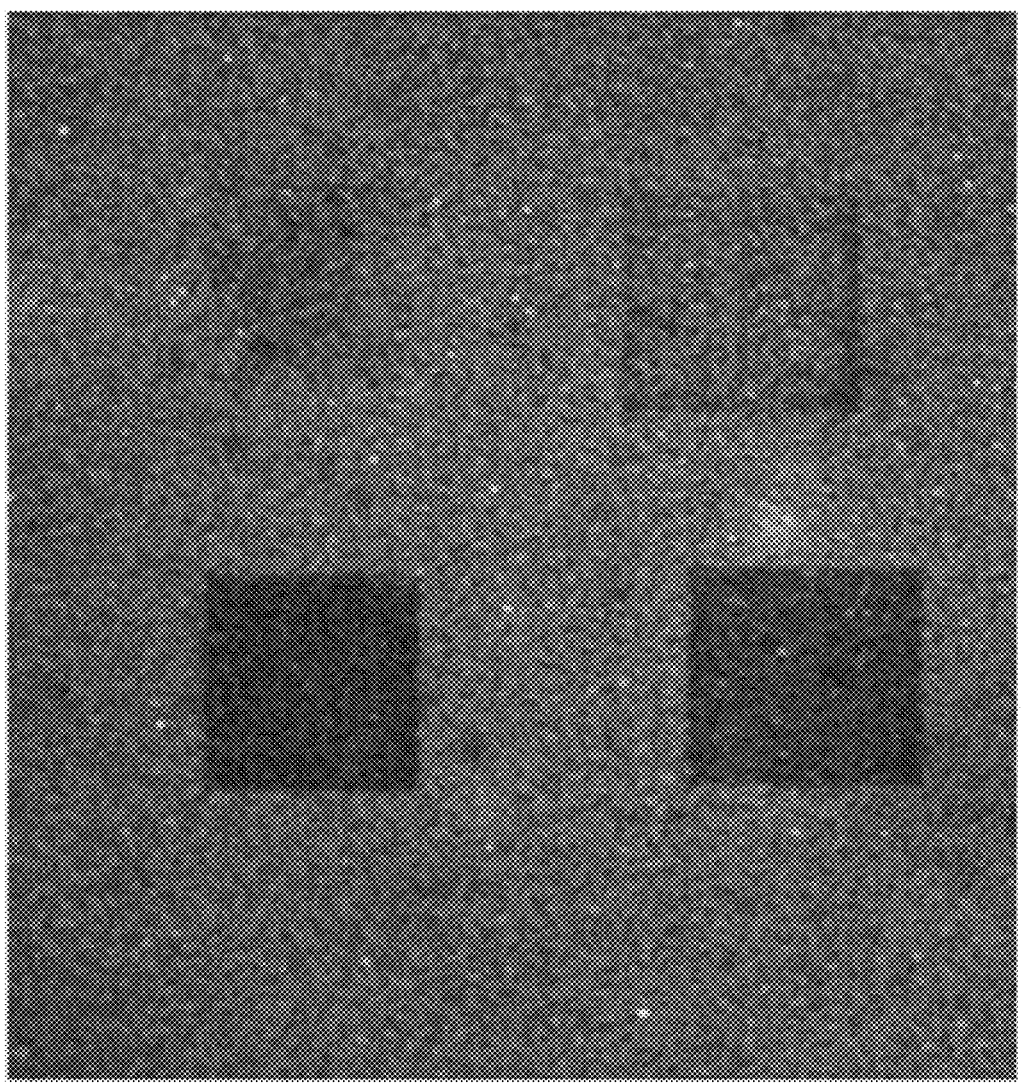
FIG. 7 is an image showing multiphoton laser-induced unbinding of fluorescently-tagged antibody from a Protein A-coated slide.

This example illustrates a multiphoton laser-induced unbinding of fluorescently tagged antibody from a Protein A-coated slide (see FIG. 7). A Protein-A coated slide was labeled with as saturating dose of cy3-conjugated anti-laminin antibody (light grey). A multiphoton laser was then used to illuminate selected areas of the slide, to unbind the antibody, allowing rebinding of a cy2-conjugated anti-laminin antibody (dark grey). All four blocks so formed received the same total two-photon excitation, but the laser intensity was higher for the top row than for the bottom row. The figure thus shows the intensity dependence of unbinding, which was greater in the top row than in the bottom row.

Example 6

Figure 8:
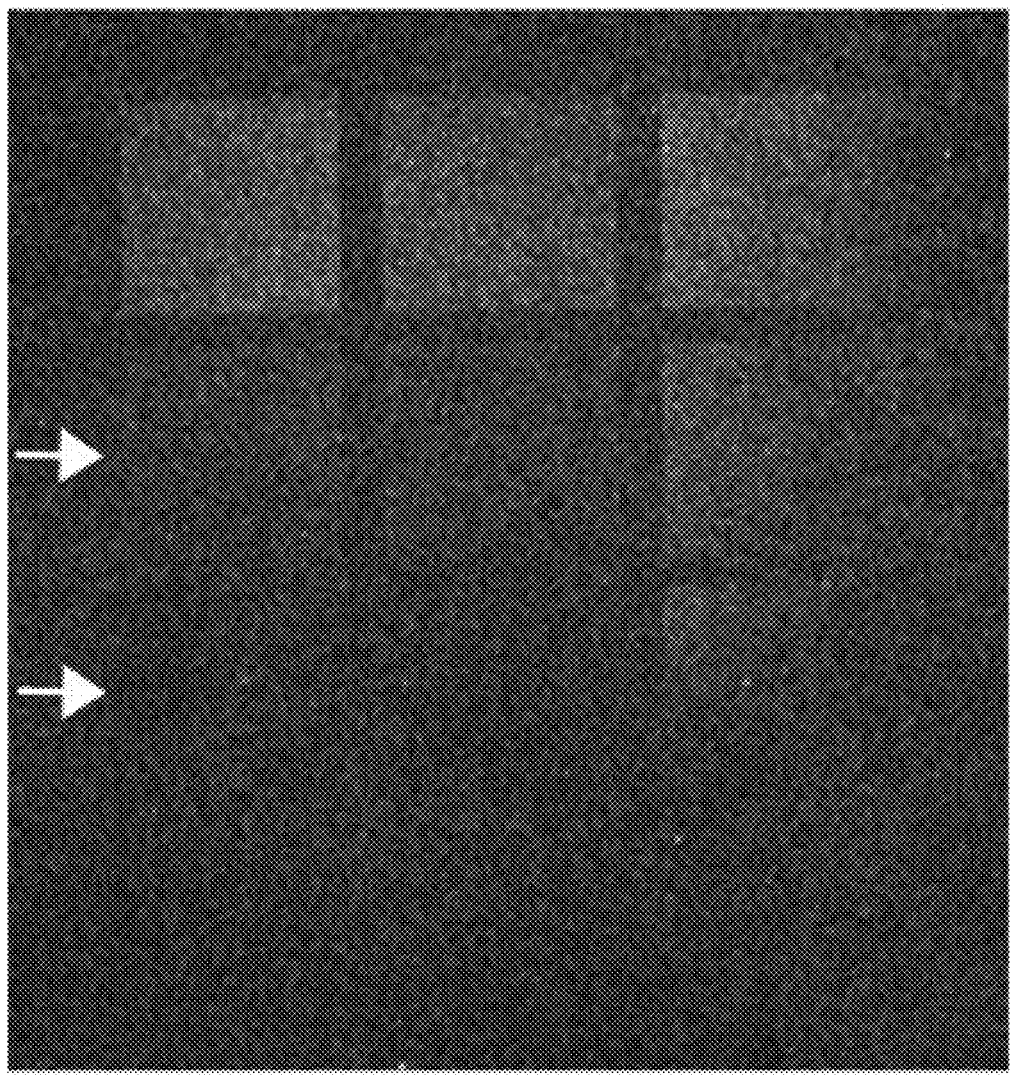
FIG. 8 is an image showing multiphoton laser-induced dehybridization of a fluorescently-tagged DNA target oligo from a complementary DNA primer oligomer.
Figure 9A:
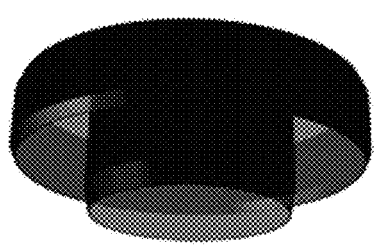
FIG. 9A-B illustrates multiple views of a culture dish and culture dish lid with dropped center and silicone seal (A) or self-filling reservoir (B) for long-term recordings of samples in culture on a micropatterned substrate according to the present disclosure.
Figure 9A:
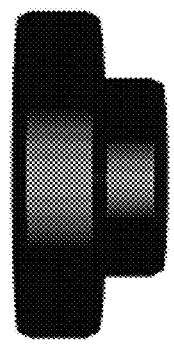
Figure 9A:
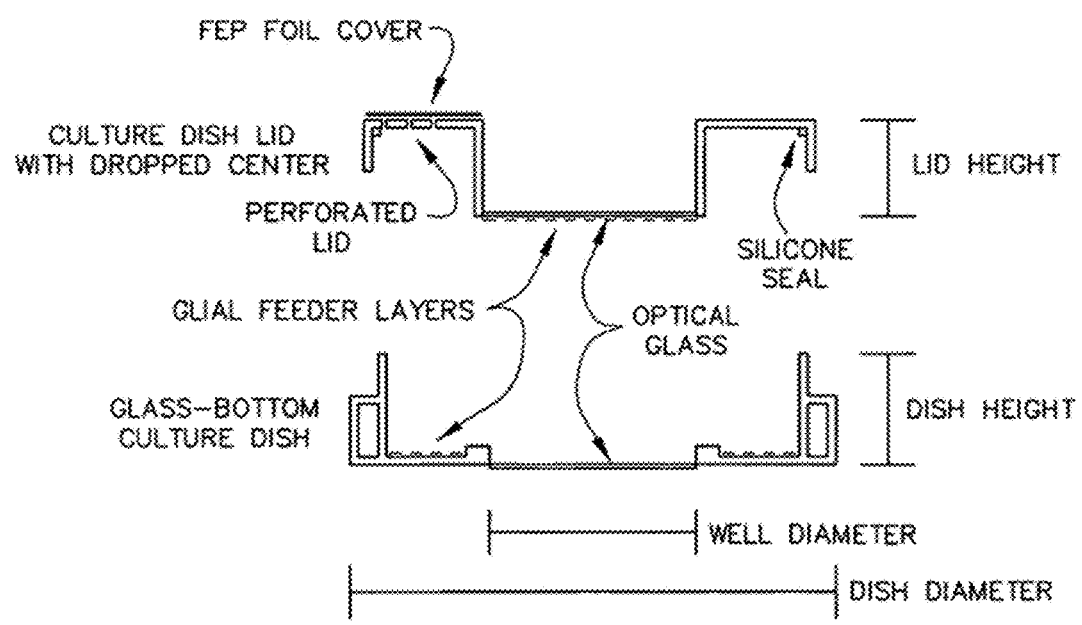
Figure 9B:
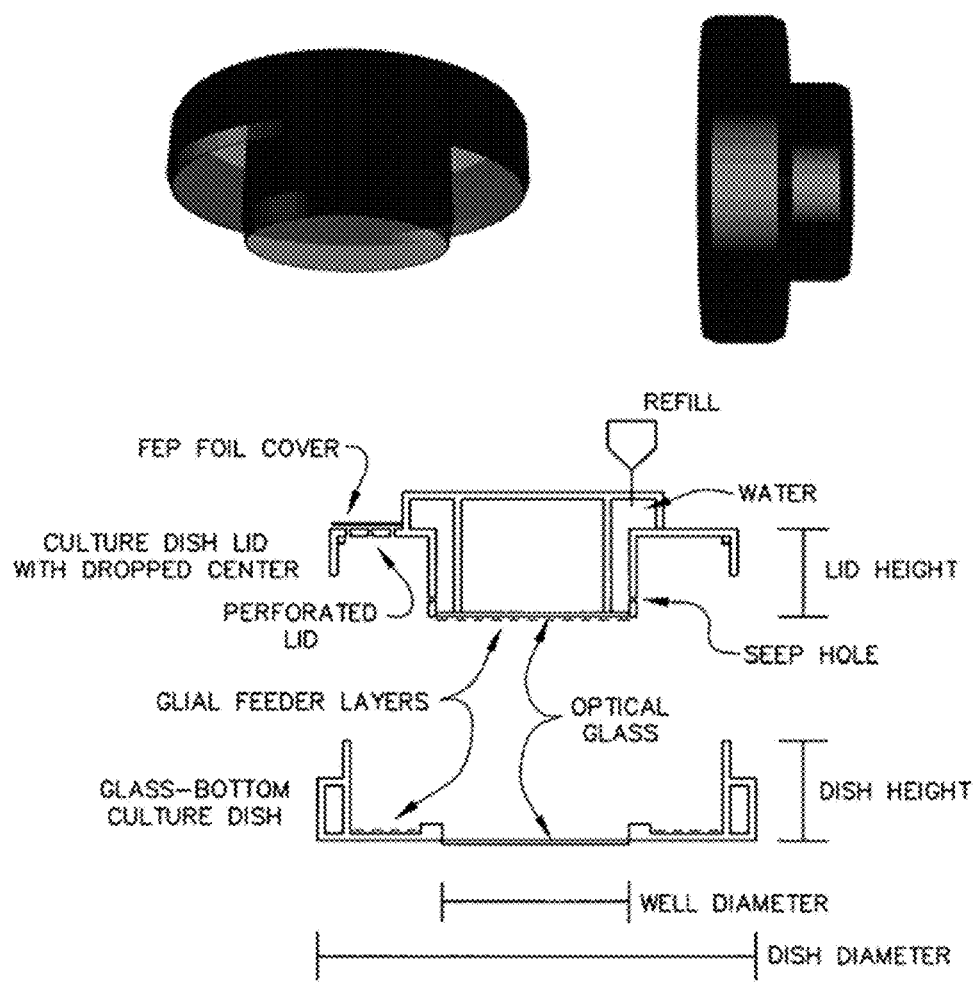

This example illustrates a multiphoton laser-induced dehybridization of a fluoresce DNA target oligomer from a complementary DNA primer oligomer (see FIG. 8). A biotin-modified DNA primer oligomer was bound to a streptavidin-coated glass slide. A cy3-modified DNA target oligomer (dark grey) was then hybridized to the primer oligomer. The target oligomer was dehybridized using, a multiphoton laser, allowing, a second, FITC-modified target oligomer (light grey) to rehybridize. The total two-photon excitation was constant at each block, but the laser intensity was halved for the second row and again for the third row, resulting in reduced dehybridization in successive rows as shown (arrows).

Example 7

This example illustrates culture dishes and culture dish lids adapted for long-term imaging of cells in culture on a micropatterned surface-modified substrate (see FIG. 9). The modified culture dish lid as shown is used together with a glass-bottom culture dish, in which a surface-modified substrate bearing cells of interest is placed for observation. The culture dish lid as modified according to the present teaching, provides for long-term observation of the behavior of the cells on the surface-modified substrate. The culture dish lid can be modified to reduce or eliminate condensation from the culture dish which can interfere with optical imaging of the cells. Evaporation of fluid can be minimized by using a membrane such as a tetrafluoroethylene-co-hexafluoropropylene, (FEP) membrane that is permeable to gas but not water vapor in addition to either (A) a water-tight seal such as a silicone seal around the inside of the lid and/or (B) a self-filling reservoir. While the dimensions of the lid and dish can vary, the dropped center can be configured so that it can be immersed in cell culture medium contained within the glass-bottomed dish, to prevent condensation on the lid in the area of the lid above the dropped center. In addition, the plastic of the lid can be removed above the dropped center, allowing transmitted light imaging without passing through plastic. The dropped center lid is adaptable to culture dishes of varying sizes as well as for use with multiwell plates.

Example 8

Figure 10:
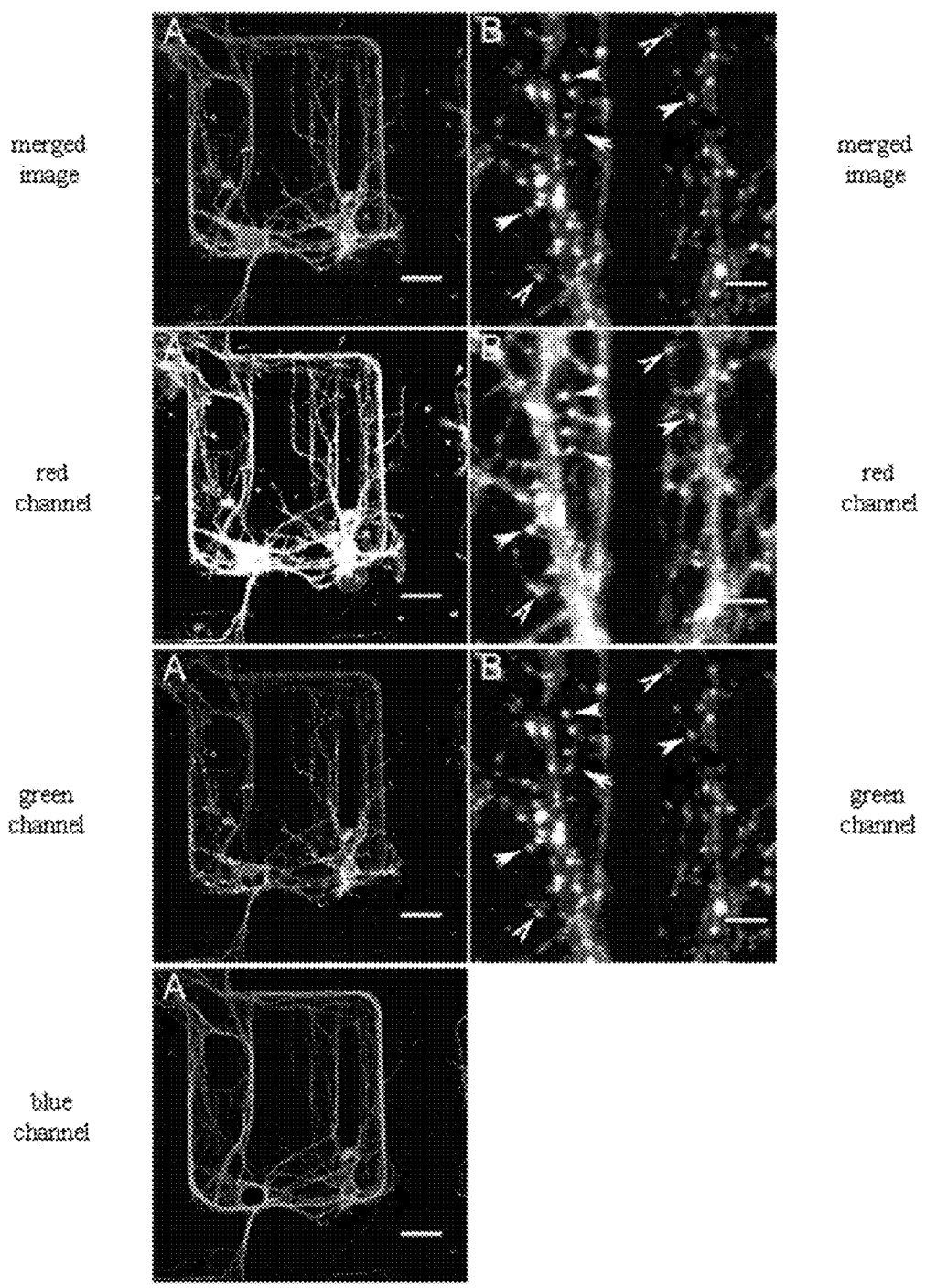
FIG. 10 illustrates hippocampal neurons, at low-magnification (A) or high-magnification (B), grown for 15 days on a substrate patterned using a multiphoton-induced release of poly-ornithine.

This example illustrates hippocampal neurons grown for 15 days on a substrate patterned using a multiphoton-induced release of PLO (see FIG. 10). (A) Cells grow on the PLO and are largely excluded from PLO-free areas of the substrate. Two cells are within the central boxed area and connect to two other cells via thin bridges (outside field). Cells were fixed and stained for immunofluorescence using antibodies to synapsin 1 (green), actin (red) and axonal specific neurofilaments (blue). (B) High magnification of a selected region showing spines (arrowheads). Actin (red) is associated with the spine, while the presynaptic terminal stains with the antibody to synapsin I (green). (A) Bar=10 μm (B) Bar=2 μm.

Example 9

Figure 11:
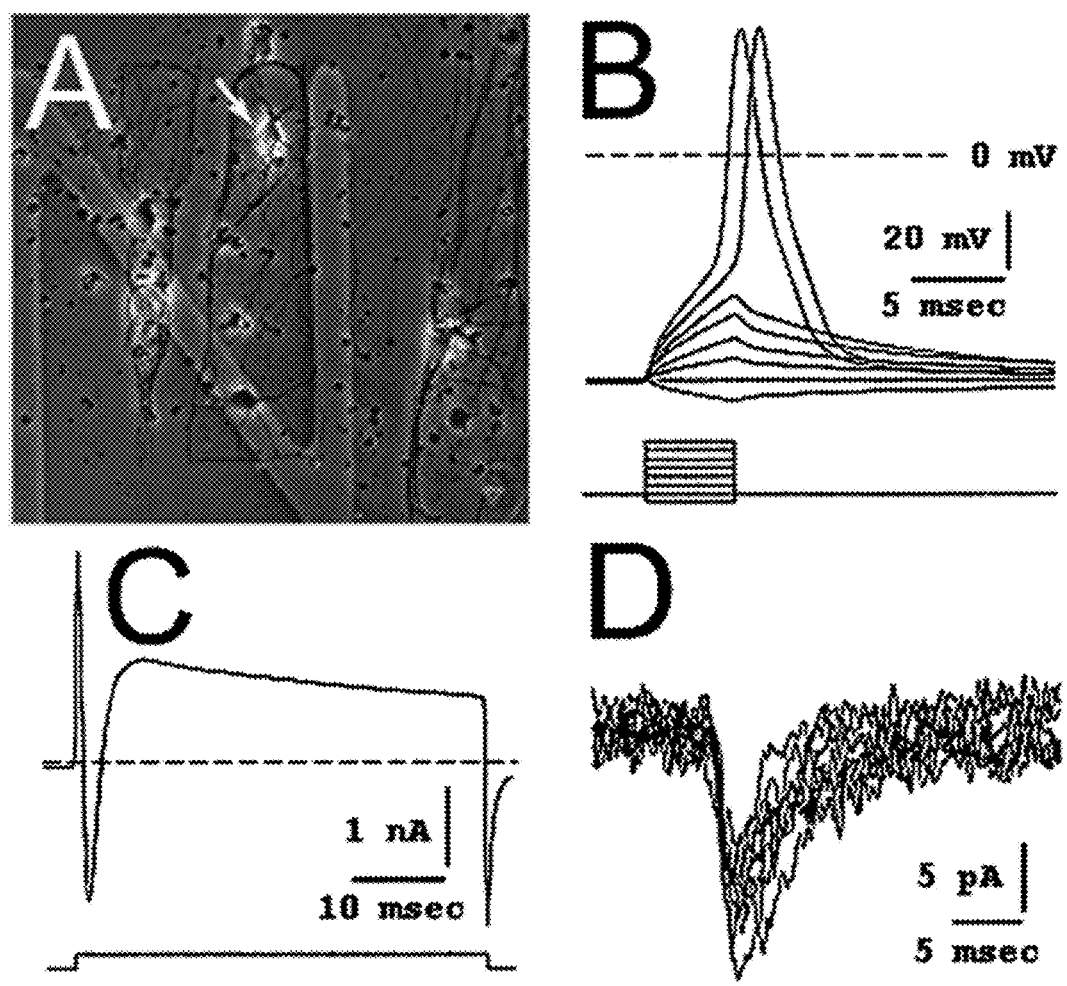
FIG. 11A-D illustrates functional synaptic connections in a 2 cell circuit at 14 days in vitro where (A) shows a phase image or the circuit, (B) shows action potentials recorded in the cell, (C) shows the inward sodium current and outward potassium current for a voltage step, and (D) shows spontaneous miniature excitatory postsynaptic currents.

This example illustrates functional synaptic connections in a 2 cell circuit at 14 days in vitro (see FIG. 11). (A) Phase image showing the 2 cell circuit (elongated region at middle of field). The arrow indicates the cell that was recorded. The second cell is at the bottom of the elongated region. (B) shows action potentials recorded in the cell under current clamp, (C) shows the inward sodium current and outward potassium current for a voltage step from −80 mV to 0 mV. (D) shows spontaneous miniature excitatory postsynaptic currents (EPSCs) recorded at −80 mV. The EPSCs are either autaptic or from the other cell.

Example 10

Figure 12:
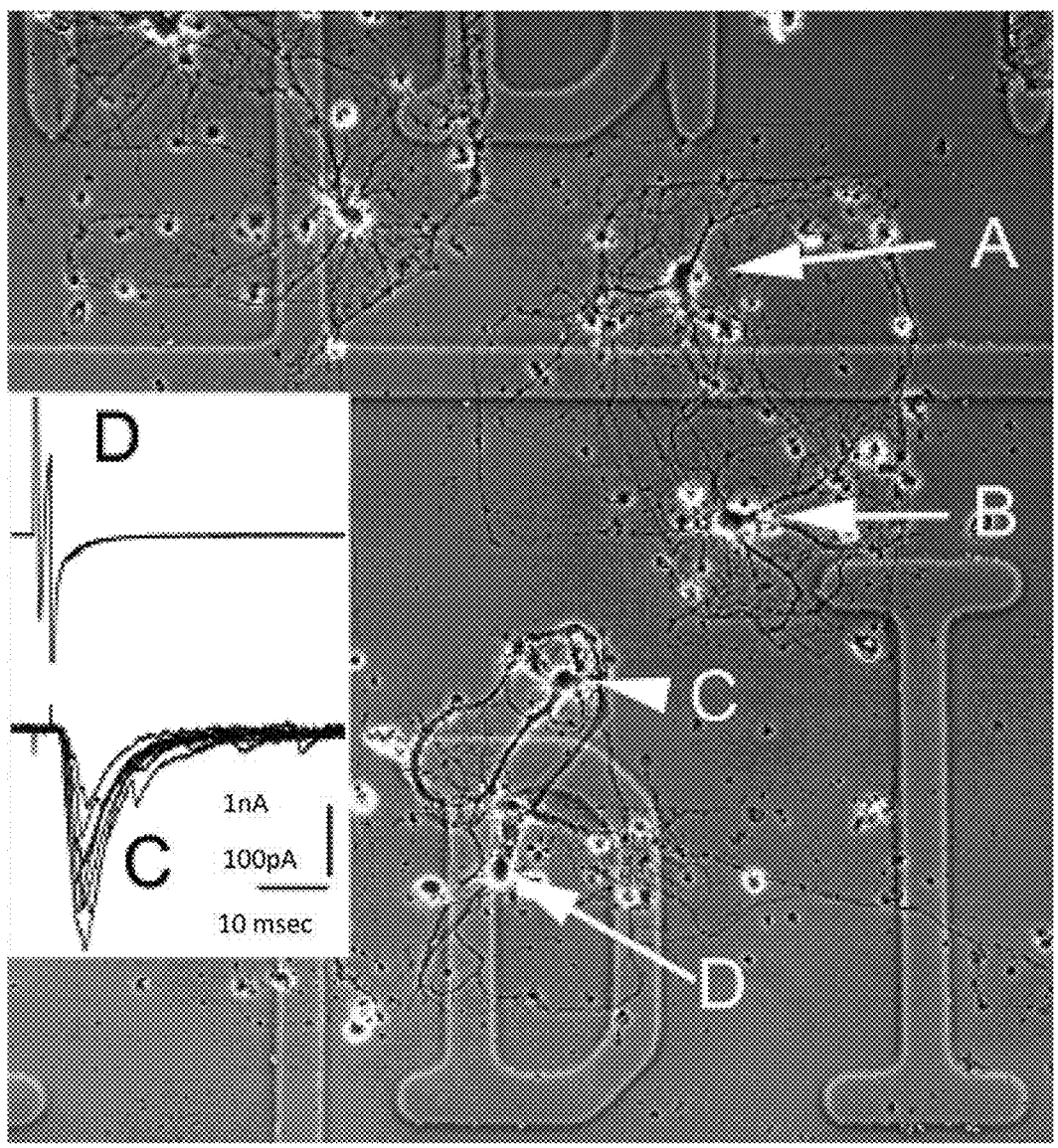
FIG. 12 illustrates functional synapses between two cells (A and B or C and D) at 10 days in vitro where the inset (C) shows an evoked postsynaptic current from a stimulation (inset D).

This example illustrates functional synapses between two cells in as 2 cell circuit at 10 days in vitro (see FIG. 12). Three two cell circuits can be seen in the phase image. Recordings were made from pairs of cells A&B, C&D and they were found to be synaptically coupled. Inset shows that stimulation of D produces evoked EPSCs in cell C. Field width=100 μm.

The present application also includes the following aspects:

Aspect 1. A substrate for cells in culture comprising a glass surface having a coating of adhesive molecules and a plurality of macromolecules bound thereto with or without a predefined multiphoton laser-induced micropattern.

Aspect 2. A multiphoton microscope for generating a micropatterned substrate, said microscope having: an objective configured for being spaced a distance from the substrate at which at least part of the substrate is within the in-focus plane of the objective; optical elements configured for directing incident light from an ultra fast pulsed multiphoton laser to discrete regions of the in-focus plane of the objective to illuminate surface portions of the substrate that are within the discrete regions; and a sensor in the return light path for generating, at least one signal representative of the light reflected or emitted from the surface portions of the substrate.

Aspect 3. A cell culture dish lid for use with a cell culture dish, said lid comprising a dropped center well configured for immersion in culture media contained in the cell culture dish when said lid is placed on the culture dish.

Aspect 4. A cell culture dish lid, comprising: (a) a dropped-center well configured for immersion in culture media contained in a cell culture dish; (b) a water-tight seal along the lid's periphery; (c) a plurality of perforations; and (d) a gas-permeable membrane covering the perforations.

Aspect 5. A cell culture dish lid in accordance with Aspect 4, wherein the gas-permeable membrane comprises tetra-fluoroethylene-co-hexafluoropropylene (FEP).

Aspect 6. A cell culture dish lid in accordance with Aspect 4, wherein the water-tight seal is a silicone seal.

Aspect 7. A cell, culture dish lid in accordance with Aspect 4, further comprising: (e) a liquid reservoir adjacent to the perimeter of the lid, wherein the reservoir is configured to supply a cell culture dish with a cell culture medium.

Aspect 8. A method of generating a pattern of macromolecules on a solid substrate comprising: dividing the in-focus plane of an objective of a multiphoton microscope into a plurality of discrete regions; directing incident, light to the discrete regions to illuminate surface portions of the solid substrate that are within the discrete regions; and unbinding a plurality of macromolecules from each surface portion associated with each discrete region, wherein the step of directing light to the discrete regions comprises serially directing light to each discrete region to separately illuminate each surface portion within a corresponding one of the discrete regions, and wherein the method further comprises binding macromolecules to the solid substrate, wherein to binding macromolecules to the substrate comprises: diluting, the macromolecules in a buffer solution; spotting the macromolecules in solution on each surface portion of the substrate that received high intensity ultrafast pulsed IR light; and processing to remove any unbound macromolecules and to block non-specific binding.

Aspect 9. A method of creating a micropattern of macromolecules on a solid substrate comprising: applying a coating of adhesive molecules to the solid substrate; binding a plurality of macromolecules to the coating of adhesive molecules; and applying incident multiphoton laser light to one or more selected surface portions of the solid substrate to unbind an amount of macromolecules from the selected surface portions to create a micropattern of macromolecules, wherein the incident laser light comprises ultrafast pulsed IR light.

All publications and patent applications cited in this specification are herein incorporated by reference in their entireties, as if each individual publication or patent application were specifically and individually indicated to be incorporated by reference.

What is claimed is:

1. A cell culture dish lid adapted for to microscope imagine of cells immersed in culture medium in a glass-bottom cell culture dish while minimizing fluid evaporation and condensation that interferes with optical comprising:
   a dropped center well comprising an optical glass planar surface configured to contact culture medium contained in a cell culture dish thereby allowing transmitted light microscope imaging of cells without the light passing through plastic;

a periphery comprising a plurality of perforations;

a membrane covering the plurality of perforations, wherein the membrane is permeable to gas but not water vapor; and a watertight seal within the lid and peripheral to the plurality of perforations, configured to seal the culture medium contained in the cell culture dish, whereby condensation that interferes with optical imaging of cells is minimized, and whereby evaporation of fluid is minimized.

2. A cell culture dish lid in accordance with claim 1, wherein the watertight seal is a silicone seal.

3. A cell culture dish lid in accordance with claim 1, wherein the membrane is a tetrafluoroethylene-co-hexafluoropropylene (FEP) membrane.

4. A cell culture dish lid in accordance with claim 1, wherein the dropped center well is cylindrical.

5. A cell culture dish lid adapted for long-term optical imaging of cells immersed in culture medium in a glass-bottom cell culture dish while minimizing fluid evaporation and condensation that interferes with optical imaging, comprising:

a dropped center well comprising an optical glass planar surface configured to contact culture medium contained in a cell culture dish thereby allowing transmitted light microscope imaging of cells without the light passing through plastic;

an inner wall;

an outer wall comprising a seep hole;

a periphery comprising a plurality of perforations; and a membrane covering the plurality of perforations, wherein the membrane is permeable to gas but not water vapor;

wherein the inner wall, the outer wall, the membrane and the planar membrane is permeable to gas but not water vapor;

wherein the inner wall, the outer wall, the membrane and the planar surface define a liquid reservoir whereby condensation that interferes with optical imaging of cells is minimized and whereby evaporation of fluid is minimized.

6. A cell culture dish lid in accordance with claim 5, wherein the dropped center well is cylindrical.

7. A cell culture dish lid in accordance with claim 5 wherein the membrane, is a tetrafluoroethylene-co-hexafluoropropylene (FEP) membrane.

\* \* \* \* \*